US00PP13342P2

(12) United States Plant Patent
Zary

(10) Patent No.: US PP13,342 P2
(45) Date of Patent: Dec. 10, 2002

(54) SHRUB ROSE PLANT NAMED 'JACSALPS'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/724,681

(22) Filed: Nov. 28, 2000

(51) Int. Cl.[7] ..... A01H 5/00
(52) U.S. Cl. ..... Plt./104
(58) Field of Search ..... Plt./104

(56) References Cited

U.S. PATENT DOCUMENTS

| | | | | | |
|---|---|---|---|---|---|
| PP7,127 | P | * | 1/1990 | Warriner | Plt./125 |
| PP8,682 | P | * | 4/1994 | Austin | Plt./104 |
| PP8,688 | P | * | 4/1994 | Austin | Plt./104 |
| PP9,716 | P | * | 12/1996 | Olesen et al. | Plt./118 |

* cited by examiner

*Primary Examiner*—Bruce R. Campell
*Assistant Examiner*—W C Baker
(74) *Attorney, Agent, or Firm*—Klarquist Sparkman, LLP

(57) ABSTRACT

Shrub rose plant having bright yellow flowers of informal form, dark green foliage resistant to rust and powdery mildew, moderately spicy scent and an ability to root easily.

1 Drawing Sheet

LATIN NAME OF GENUS AND SPECIES

*Rosa hybrida.*

VARIETY DENOMINATION

JACsalps.

SUMMARY OF THE INVENTION

The present invention relates to a new and distinct variety of rose plant of the shrub class which was originated by me by crossing the variety JACyim, U.S. Plant Pat. No. 7,127, with the variety POULsun, U.S. Plant Pat. No. 9,716.

BACKGROUND OF THE INVENTION

The primary objective of this breeding was to produce a new rose variety having the vigorous growth, dark foliage and bright yellow flower color of the female parent combined with the larger flower size and informal flower form of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Bright yellow flower color;
2. Informal flower form;
3. Dark green foliage;
4. Resistance to rust and powdery mildew;
5. Moderately spicy scent; and
6. Ability to own root easily.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

The female parent, JACyim, has smaller flowers than JACsalps whereas the male parent has larger flowers than JACsalps.

COMPARISON WITH SIMILAR VARIETY

JACyelsh, U.S. Plant Pat. No. 10,283, a similar miniature variety, has a smaller, more compact plant with flowers of twenty petals as compared to the seventy to eighty petals of JACsalps flowers.

BRIEF DESCRIPTION OF THE ILLUSTRATIONS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—JACyim (U.S. Plant Pat. No. 7,127).
*Pollen parent.*—POULsun (U.S. Plant Pat. No. 9,716).
Classification:
*Botanical.*—*Rosa hybrida.*
*Commercial.*—Shrub.

FLOWER

Observations made from specimens beginning at two years of age grown in a garden environment at Somis in California, January, 1999 to July, 2000. Typical light levels range from 800 to 10,000 candles. Daylight ranges from 10 to 14 hours and temperatures range from 35° F.–100° F.

Blooming habit: Continuous.

Bud:

*Size.*—One-half inch long and 1½ inches in diameter when the petals start to unfurl.

*Form.*—The bud form is short, globular.

*Color.*—When sepals first divide, bud color is Yellow Group 8C. When half blown, the upper sides of the petals at the center of the flower are Yellow Group 8B; in the middle they are Yellow Group 8C, and in the outer third they are Yellow Group 8D; and the lower sides of the petals are Yellow Group 8A on the center petals; the outer petals are Yellow Group 8A on their lower third, Yellow Group 8B on the middle third and fade to Yellow Group 8C on their outer third.

*Sepals.*—Color: Upper surface: Green Group 138B. Lower surface: 139D. Length: ½ inch. Width: ¼ inch. Surface texture: Covered in fine hairs. There are three lightly appendaged sepals that also have glands on the sepal edges. There are two unappendaged sepals with hairy edges.

*Receptacle.*—Color: Green Group 137D. Shape: Funnel. Size: Medium, about ¼"×¼". Surface: Smooth, with a few very fine hairs.

*Peduncle.*—Length: Short, averaging about 1¼ inches. Surface: Smooth, with a few very fine hairs. Color: Yellow-Green Group 146B. Strength: Stiff, erect, slender.

Bloom:

*Size.*—Small. Average open diameter is 2¾ inches.

*Borne.*—Several together in pyramidal clusters of five to thirteen blooms.

*Stems.*—Strength: Strong. Average length available for use as cut flowers is about twelve to fourteen inches.

*Form.*—When first open: Bloom is cupped, well filled with petals. Permanence: Retains its form to the end.

*Petalage.*—Number of petals under normal conditions: 70–80.

*Color.*—The upper sides of the petals are Yellow Group 8B on the center petals; the middle petals are Yellow Group 8C while the outer petals are Yellow Group 8C except on the outer edges where they are Yellow Group 8D. The reverse sides of the petals are Yellow Group 8A on the center petals; the outer petals are Yellow 8A on their lower third, Yellow Group 8B in the middle and Yellow Group 8C on the outer third. The base of each petal has a small (1/32"×1/32") bright Yellow Group 7A color spot. The major color on the upper side is Yellow Group 8B.

*Variegations.*—There is an occasional Green Group 143D streak on the outer petals.

*Discoloration.*—The general tonality at the end of the first day: Little change. At the end of the third day: A general change from Yellow Group 8B in the flower center to Yellow Group 8C over the entire flower.

*Fragrance.*—Moderate. Spicy.

Petals:

*Texture.*—Thin.

*Size.*—Length: 15/16 inch–1¼ inch. Width: ¼ inch–⅝ inch.

*Shape.*—Obovate to oblanceolate.

*Form.*—Flat to slightly curved.

*Arrangement.*—Irregular. Petaloids in the center are many, Yellow Group 8B in color and ¼–½ inch long, ⅛ inch wide.

*Persistence.*—Petals drop off cleanly before drying.

*Lastingness.*—On the plant: Fair (about 5–6 days). As a cut flower: Fair (about 6 days).

Reproductive parts:

*Anthers.*—Size: Small. Quantity: Very few, 0–5 anthers. Color: Greyed-Orange Group 177A. Arrangement: Mixed with petaloids.

*Filaments.*—Color: Yellow Group 8A.

*Pollen.*—Color: No pollen has been observed to shed from the anthers.

*Styles.*—Color: Green Group 138D.

*Stigmas.*—Color: Green-White Group 157A.

*Hips.*—None observed.

Plant:

*Form.*—Shrub.

*Growth.*—Vigorous, medium, upright and branching. At maturity, height is 3½ feet high, width is 2½ feet high (one year old, in the garden without pruning).

Foliage: Number of leaflets on normal mid-stem leaves: 5 or 7.

*Size.*—Medium (4½ inches long×3½ inches wide).

*Quantity.*—Abundant.

*Color.*—New foliage: Upper and lower surfaces: Greyed-Purple Group 183A. Old foliage: Upper surface: Green Group 135A. Lower surface: Green Group 137C.

Leaflets:

*Shape.*—Ovate. Base: Rounded. Apex: Acute.

*Texture.*—Leathery, glossy.

*Edge.*—Serrated.

*Serration.*—Single, small.

*Petiole rachis.*—Color: Green Group 137D.

*Petiole underside.*—Rough with prickles.

*Stipules.*—Long and serrated (about ½"–¾").

*Disease resistance.*—Resistant to mildew and rust, susceptible to blackspot under normal growing conditions.

Wood:

*New wood.*—Color: Yellow-Green Group 146C. Bark: Smooth.

*Old wood.*—Color: Green Group 137C. Bark: Smooth.

Prickles:

*Quantity.*—On main canes from base: 3 to 5 prickles per five inches of stem. On laterals from main canes: 3 to 5 prickles per five inches of stem.

*Form.*—Medium, straight with a slight hook upward.

*Color when young.*—Yellow-Green Group 147C with Greyed-Purple Group 183A at the base of the prickle.

*Color when mature.*—Greyed-Orange Group 168D.

Small prickles:

*Quantity.*—On main stalks: None. On laterals: None.

I claim:

1. A new and distinct variety of rose plant of the shrub class, substantially as herein shown and described, characterized particularly by its bright yellow flower color and informal flower form, its dark green foliage resistant to rust and powdery mildew, moderately spicy scent and ability to root easily.

* * * * *

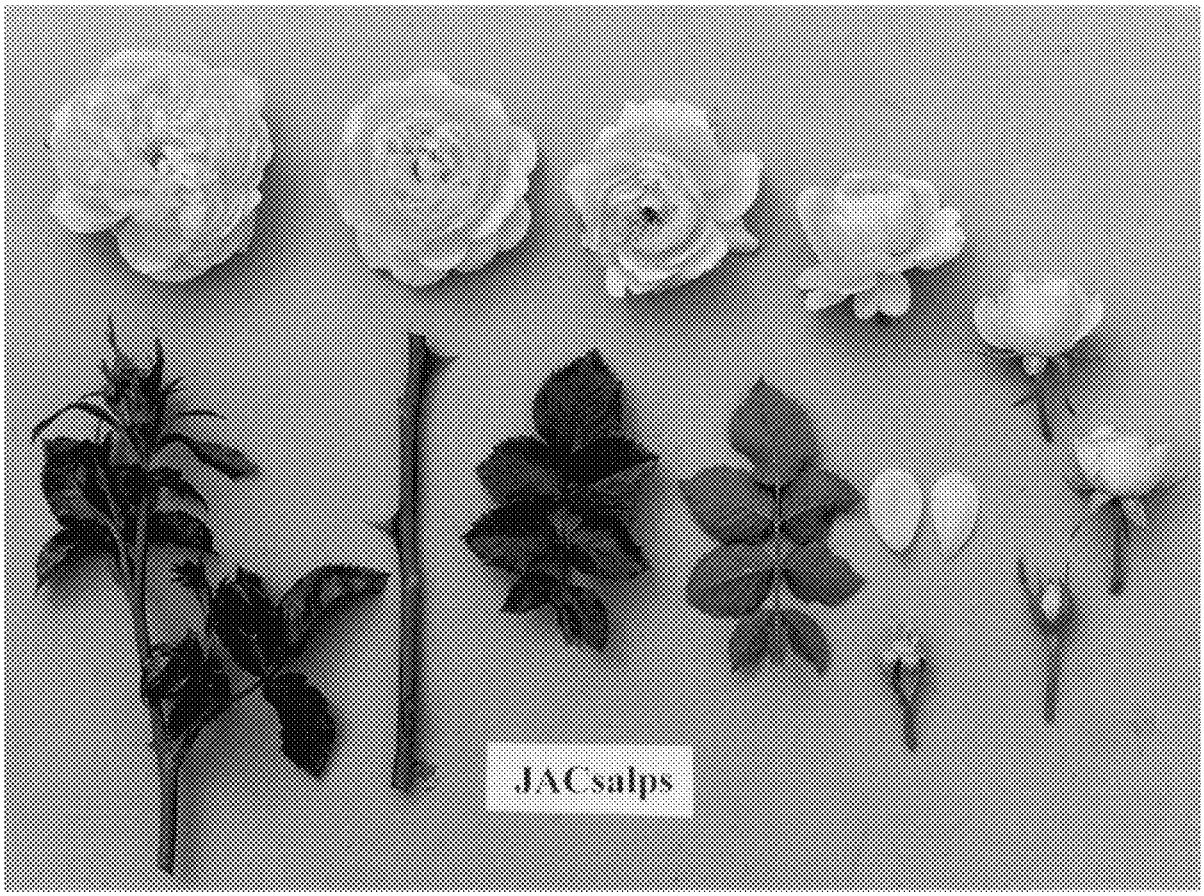
JACsalps